US00PP17369P2

(12) United States Plant Patent
Lemon

(10) Patent No.: US PP17,369 P2
(45) Date of Patent: Jan. 16, 2007

(54) ***GERANIUM* PLANT NAMED 'PATRIOT SOFT PINK'**

(50) Latin Name: *Pelargonium×hortorum*
Varietal Denomination: Patriot Soft Pink

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 10 days.

(21) Appl. No.: 11/177,067

(22) Filed: Jul. 8, 2005

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent Bell
*Assistant Examiner*—Annette H Para
(74) *Attorney, Agent, or Firm*—The Webb Law Firm

(57) ABSTRACT

'Patriot Soft Pink' is a new variety of *geranium* that exhibits free flowering, good outdoor performance, and bright clear pink flowers.

1 Drawing Sheet

Botanical classification: *Pelargonium×hortorum.*
Varietal denomination: 'Patriot Soft Pink'.

BACKGROUND OF THE INVENTION

The present invention comprises a new and distinct cultivar of *Pelargonium×hortorum* known by the varietal name 'Patriot Soft Pink'. The new variety was discovered in Lompoc, Calif. The new variety is a result of cross breeding Light Pink Seedling #6729 (female parent) (unpatented) and Light Pink Seedling #6123 (male parent) (unpatented). The purpose of the breeding program was to introduce a geranium having good outdoor performance. The new variety is similar in plant type to its female parent, but is more free flowering. The new variety is similar in flower color to its male parent, but is more compact. 'Patriot Soft Pink' is also similar in flower color to 'Rocky Mountain Light Pink' (to the best of breeder knowledge, non patented or the subject of a pending application), but has a more compact growth habit. The good outdoor performance and free flowering nature of 'Patriot Soft Pink' distinguishes the new variety from other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. using full light, 16° C. night temperature, 20° C. day temperature, and grown in a soilless media with constant fertilizer at 200–250 ppm nitrogen and potassium. The new variety exhibits developed roots at 17 days at an average temperature of 23° C. and has a response time of seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
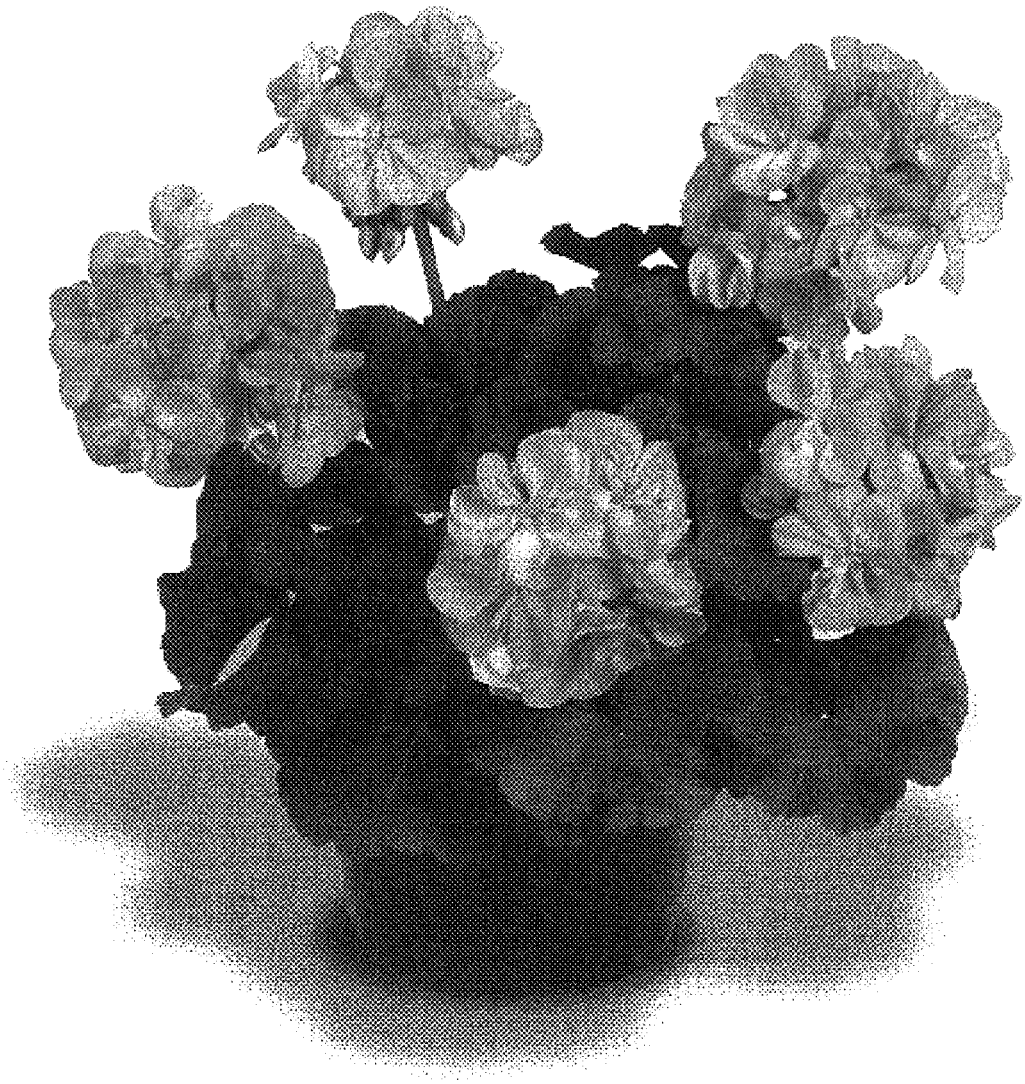

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S. Colour Chart of The Royal Horticultural Society of London.

PLANT

Market class: Zonal.
Time to initiate roots: Approximately 5–7 days at about 23° C.
Time to develop roots: Approximately 17 days at about 23° C.
Time to produce a finished flowering plant from a rooted cutting: About 7 weeks in a 10 cm. container.
Rooting habit: Good, normal.
Form: Round-mounded.
Height from media surface to top of foliage: 11.0–13.0 cm.
Height from media surface to top of flowers: 25.0–27.0 cm.
Plant diameter: 22.0–23.0 cm.
Vigor: 4 on a scale of 5.
Strength: No artificial support is needed.
Branching habit: Free branching.
Stem:
- *Main stem length.*—8.0–11.0 cm.
- *Diameter.*—0.7 cm.
- *Color.*—Yellow-Green Group 144A.
- *Texture.*—Leathery texture.
- *Pubescence.*—Slight.
- *Internode length.*—1.0–1.5 cm.

Lateral branches:
- *Length.*—Primary: 5.0–8.0 cm. Secondary: Plant is too young to measure.
- *Diameter.*—Primary: 0.5–0.6 cm. Secondary: Plant is too young to measure.
- *Internode length.*—1.0–1.5 cm.
- *Texture.*—Leathery.
- *Pubescence.*—Slight.
- *Color.*—Yellow-Green Group 144A.

Foliage:
- *Arrangement.*—Alternate.

*Stipules.*—Number: 2 at every node. Size: 0.5–0.9 cm wide. Color: Yellow-Green Group 144A.

*Zone.*—Location: From outer edge of leaf to ½ of the way toward the center. Color: Green Group 137A.

*Size of leaf.*—Length: 6.0–9.8 cm. Width: 7.7–12.2 cm.

*Shape of leaf* (*generally*).—Reniform with a stalked base.

*Shape of apex.*—Rounded in accordance with reniform leaf shape.

*Shape of base.*—Cordate.

*Texture.*—Velvety.

*Aspect.*—Leaves have a very slight slope increasing from point of connection toward the margin.

*Margin type.*—Crenate.

*Pubescence.*—Upper surface: Moderate. Lower surface: Moderate.

*Color.*—Young leaves: Upper surface: Green Group 137C. Lower surface: Green Group 138B. Mature leaves: Upper surface: Green Group 137B. Lower surface: Green Group 137C.

*Petiole.*—Length: 5.6–10.2 cm. Diameter: 0.25–0.3 cm. Color: Yellow-Green Group 144A.

*Veins.*—Venation type: Palmate. Color: Upper surface: Green Group 138B. Lower surface: Yellow-Green Group 145B.

INFLORESCENCE

Bud:

*Stage of development when bud characteristics determined.*—Bud shows color at side but sepals are not parting at the tips.

*Shape of cluster.*—Elliptical.

*Diameter of cluster.*—2.4–2.6 cm.

*Number of buds per cluster.*—16–24.

*Shape of individual bud.*—Ellipse.

*Length of individual bud.*—0.9–1.0 cm.

*Width of individual bud.*—0.6–0.7 cm.

Natural flowering season at specified location(s): Year round horticultural greenhouse crop.

Blooming habit: Continuous and free flowering.

Umbel diameter: 9.3–3.3 cm.

Umbel depth: 6.8–7.9 cm.

Borne: Umbel, flowers on pedicel, pedicel on peduncle.

Inflorescence position: Above foliage.

Number of inflorescences per lateral branch: 1–2.

Lastingness of an individual flower: 10–14 days.

Florets:

*Form.*—Flat and slightly cupped. As flowers mature, the florets gradually become more open/flat.

*Number per umbel.*—20–42.

*Diameter.*—3.7–5.5 cm.

*Depth.*—1.8–2.0 cm.

Petals:

*Color.*—The top two petals of the floret have a pronounced white eye as compared to the bottom petals. Upper surface: The top two or three petals are Red-Purple Group 68C. The bottom one third of the petals fades to Red-Purple Group 68D and then immediately to White Group 155D. The point of connection then immediately fades to White Group 155D. The venation is Red-Purple Group 73B. The bottom petals are Red Group 68C and fade to White Group 155D at the pointed base. The venation is Red-Purple Group 73B. Lower surface: The top petals have a margin of Red-Purple Group 68D that fades to Red-Purple Group 73D as it approaches the center of the petal. The bottom one third of the petal fades to White Group 155D. The venation is Red-Purple Group 65C. The bottom petals have a margin of Red-Purple Group 68D that fades to Red-Purple Group 73D and then to White Group 155D and remains as White Group 155D to the point of connection.

*Shape.*—Inverted teardrop.

*Length.*—2.5–2.8 cm.

*Width.*—2.2–2.6 cm.

*Apex shape.*—Smooth and rounded.

*Base shape.*—Tapered to a point.

*Margin.*—Entire; smooth.

*Number per floret.*—5–8.

*Texture.*—Smooth.

*Tonality from a distance.*—Bright clear pink flowers atop of mounding medium green foliage.

Petaloids:

*Quantity.*—0–2 per floret.

*Shape.*—Splits in a two pronged unit or are tubular.

*Color* (*upper and lower surface*).—The upper surface is Red-Purple Group 73C and fades to white at the petal base. The lower surface of the petal is Red-Purple Group 73D and fades to white at the petal base.

*Length.*—0.9–1.4 cm.

*Width.*—0.3–0.9 cm.

Pedicel:

*Length.*—2.1–2.6 cm.

*Diameter.*—0.13–0.15 cm.

*Color.*—A highlight of Greyed-Purple Group 180A where the pedicel connects to the floret and fades quickly to Yellow-Green Group 144A.

Peduncle:

*Length.*—16.5–23.8 cm.

*Diameter.*—0.25–0.45 cm.

*Texture.*—A slightly rough leather texture with a slight to moderate amount of pubescence.

*Color.*—Yellow-Green Group 144A.

Sepal:

*Number.*—5.

*Pubescence.*—Moderate.

*Shape.*—Lanceolate.

*Width.*—0.20–0.39 cm.

*Length.*—0.9–1.0 cm.

Fragrance: No unusual fragrance.

Disease resistance: None observed.

Temperature tolerance: None observed.

Drought tolerance: None observed.

REPRODUCTIVE ORGANS

Stamens:

*Number* (*per flower*).—9–11.

*Filament.*—Length: 0.7–0.9 cm. Color: White Group 155D with the tip being Red-Purple Group 66C.

*Anthers.*—Shape: Oval-like with a slight curve. Length: 0.2–0.25 cm. Color: Greyed-Red Group 180B.

*Pollen.*—Color: Greyed-Orange Group 169B. Amount (generally): Plentiful.

Pistils:

*Number.*—1.

*Length.*—0.9 cm.

*Style.*—Length: 0.3 cm. Color: Red-Purple Group 63A.

*Stigma.*—Shape: Style splits and radiates into 5 parts. Color: Red-Purple Group 63A. Size: 0.15 cm high.

*Ovaries.*—Position: Superior. Pubescence: Present. Length: 0.45 cm. Width: 0.15–0.2 cm. Color: Yellow-Green Group 144A.

I claim:

1. A new and distinct variety of *geranium* named 'Patriot Soft Pink' as described and illustrated.

* * * * *